United States Patent
Tajima et al.

(10) Patent No.: US 7,176,020 B2
(45) Date of Patent: Feb. 13, 2007

(54) EBV-INFECTED STOMACH CANCER CELL LINE

(75) Inventors: Masako Tajima, Tokyo (JP); Masakatsu Takanashi, Tokyo (JP); Yukihisa Miyazawa, Tokyo (JP); Toshio Takeshima, Tokyo (JP); Kota Okinaga, Tokyo (JP)

(73) Assignee: Eisai Co., Ltd., Tokyo (JP)

( * ) Notice: Subject to any disclaimer, the term of this patent is extended or adjusted under 35 U.S.C. 154(b) by 639 days.

(21) Appl. No.: 10/320,608

(22) Filed: Dec. 17, 2002

(65) Prior Publication Data

US 2003/0092084 A1    May 15, 2003

Related U.S. Application Data

(62) Division of application No. 09/882,034, filed on Jun. 18, 2001, now Pat. No. 6,551,823, which is a division of application No. 09/385,467, filed on Aug. 30, 1999, now Pat. No. 6,258,598.

(30) Foreign Application Priority Data

Feb. 4, 1999    (JP)    ................................. 11-27531

(51) Int. Cl.
*C12N 5/00*    (2006.01)
*C12N 7/00*    (2006.01)
*C12N 5/08*    (2006.01)

(52) U.S. Cl. .................... 435/325; 435/235.1; 435/366

(58) Field of Classification Search ................ 435/5, 435/325, 235.1, 366, 371; 530/300, 350
See application file for complete search history.

(56) References Cited

OTHER PUBLICATIONS

Imai S et al. Journal of Virology 72(5): 4371-4378, 1998.*
Shannon-Lowe CD et al. Proc. Natl. Acad. Sci. USA 103(18): 7065-7070, 2006.*
Imai et al., J. of Virology, vol. 72, No. 5 (1998) pp. 4371-4378.
Borza et al., J. of Virology, vol. 72, No. 9 (1998) pp. 7577-7582.
Tajima et al., Jpn. J. Cancer Res., vol. 89 (1998) pp. 262-268.
Imai et al., Proc. Natl. Acad. Sci. USA, vol. 91 (1994) pp. 9131-9135.
Shousha et al., J. Clin. Pathol., vol. 47 (1994) pp. 695-698.
Pathmanathan et al., New England J. of Medicine, vol. 333, No. 11 (1995) pp. 693-698.
Epstein et al., Lancet, vol. 1, (1964) pp. 252-253.
Tajima et al., Rinsho to Virus, vol. 25, No. 3 (1997) pp. 169-176. Entire Document in Japanese. Japanese document not considered.

* cited by examiner

Primary Examiner—Alana M. Harris
Assistant Examiner—David Humphrey
(74) Attorney, Agent, or Firm—Birch, Stewart, Kolasch & Birch, LLP.

(57) ABSTRACT

An EBV strain infecting epithelial cells and a stomach cancer cell line cancerated by EBV are established to clarify the mechanism of canceration of epithelial cells into stomach cancer by EBV and to develop a chemotherapeutic agent for stomach cancer cancerated by EBV. Further, a stomach cancer cell line stably producing EBV-related antigens is established to develop a diagnostic drug for stomach cancer cancerated by EBV. According to the present invention, GTC-4 cell line was established through culture of stomach cancer tissues. GTC-4 produced the EBV strain infecting epithelial cells and simultaneously produced EBV-related antigens stably in the supernatant.

1 Claim, 1 Drawing Sheet

EBV-INFECTED STOMACH CANCER CELL LINE

This application is a divisional application of application Ser. No. 09/882,034, filed on Jun. 18, 2001 now U.S. Pat. No. 6,551,823, which is a divisional application of application Ser. No. 09/385,467, filed Aug. 30, 1999, now U.S. Pat. No. 6,258,598, the entire contents of which are hereby incorporated by reference and this application claims priority under 35 U.S.C. § 119 of application No. 11-27531 filed in Japan on Feb. 4, 1999.

BACKGROUND OF THE INVENTION

1 Field of the Invention

The present invention relates to a method of establishing an EBV-infected stomach cancer cell line from stomach cancer tissues infected with EBV, as well as EBV infecting cultured epithelial cells.

2. Description of the Related Art

EBV (Epstein-Barr Virus) is a DNA virus belonging to the family of human herpes virus. When adult persons are first infected with it, infectious mononucleosis (IM) occurs, but in Japan, the majority of persons are first infected latently with the virus at the infant stage, and through life, latent infection continues. Accordingly, this virus has been suspected to be that causing many diseases including various cancers and autoimmune diseases, but there are many features unrevealed except that the connection with Burkitt lymphoma in Africa (Epstein M A, Barr Y M, Lancet Vol. 1:252–253, 1964) and upper pharyngeal cancer in the southern part of China (Pathnabathan R. et al., New Engl. J. Med. 333(11):693–698, 1995) was proven.

In recent years, an EBV gene was detected in stomach cancer cells (Shousha S. et al., J. Clin. Pathol 47:695–698, 1994) and further the EBV gene was found to be monoclonal (Imai S. et al., Proc. Natl. Acad. Sci. USA, 91:1931–1935, 1994), and since it was suggested that the EBV gene may be involved in the canceration process, it came to be thought that EBV is involved in at least a part of stomach cancers.

At present, no diagnostic method has been established for specifying whether EBV is involved in canceration in each patient with stomach cancer, so it is not known whether the stomach cancer caused by EBV, as compared with other stomach cancers, has distinct characters such as ease of metastasis, rapidness of the progress, drug sensitivity etc. While establishment of a diagnostic method therefor is desired, establishment of a therapeutic method and particularly development of chemotherapy for stomach cancer in which EBV is involved are important tasks. For establishment of a diagnostic method and development of a chemotherapy, establishment of a stomach cancer cell line cancerated by EBV is essential.

Recently, the present inventors reported establishment of epithelial cells GT38 & GT39 derived from stomach normal tissues in patients with stomach cancer (Tajima M. et al., Jpn. J. Cancer Res. 89:262–268, 1998).; It was surprising that EBV whose natural host is lymphoid B cells infects epithelial cells to produce EBV-related antigens though in a small amount, but for establishment of the diagnostic method and development of the chemotherapy, it was desired to establish a stomach cancer cell line which was established not from normal tissues but from cancer tissues, that is, a stomach cancer cell line which certainly underwent in vivo canceration.

Further, if canceration occurs due to a product of the EBV gene, a new type of anticancer drug inhibiting the mechanism of canceration can be developed. To analyze the mechanism of canceration of stomach cancer by EBV, it would be necessary to infect epithelial cells with EBV in order to analyze which gene in EBV is involved in the canceration.

However, it was not possible to efficiently infect cultured epithelial cells with EBV in vitro, although the relationship between EBV and the stomach cancer was believed, since the EBV gene was also found in vivo in epithelial cells of stomach cancer cells etc. (Shousha S. et al., J. Clin. Pathol. 47:695–698, 1994). Up to now, it is has been reported that genetic recombinant EBV was prepared for infecting cultured epithelial cells with EBV (Borza C M et al., J. Virol. 72(9):7577–82, 1998; Imai S. et al., J. Virol. 72(5):4381–8, 1998). In these reports, a method of amplifying and capturing a very rare phenomenon, that is, a method of infecting the cells with EBV having a drug resistance gene ($Neo^r$) inserted into it followed by selection with the drug (neomycin), was used. For example, in the report of Imal in 1998, it was reported that upon infection of a culture supernatant (400,000 cells), 32 cells at the maximum were successfully infected, and there is no guarantee that such a rare phenomenon reflects naturally occurring infection with EBV. Up to now, there is no report on efficient infection of epithelial cells with EBV whose gene is not subjected to recombination, but a system for infection of epithelial cells with EBV whose gene is not modified is necessary to analyze the mechanism of actually occurring in vivo canceration by EBV.

In an epidemiological study, it was found that the antibody titer toward EBV-related antigens i.e. viral capsid antigen (VCA) and latent membrane protein (LMP) in patients with stomach cancer is higher than in healthy persons (Masako Tajima, "Rinsho To Virus" (Clinics and Virus), Vol. 25, No. 3:169–176, 1997), and the relationship between the stomach cancer and EBV was thus supported, and simultaneously the worth of diagnosis of the antibody titer toward EBV-related antigens came to attract attention.

To utilize the EBV-related antigens in diagnosis of stomach cancer, a stable supply of EBV-related antigens is essential. In consideration of posttranslational modification of proteins, cells producing EBV-related antigens are desirably epithelial cells, particularly stomach cancer cells. However, generally known EBV-infected cells such as B95-8 and Daudi are lymphoid cells and have the problem of low production of VCA and LMP. Further, GT38 & CT39 established from normal tissues in patients with stomach cancer, reported recently by the present inventors (Tajima M. et al., Jpn. J. Cancer Res. 89:262–268, 1998), had the problem of low production of VCA and LMP, as well. Further, depending on culture conditions, differentiation and induction occurred in these cells, so there was the problem of unstable production of EBV-related antigens. It was desired that a stomach cancer cell line stably producing EBV-related antigens is established from stomach cancer tissues considered to have stable traits at the final stage of canceration.

SUMMARY OF THE INVENTION

The object of the present invention is to establish an EBV infected stomach cancer cell line for stable production of EBV-related antigens used in screening of a chemotherapeutic agent and a diagnostic agent and to establish an EBV strain efficiently infecting epithelial cells, in order to develop a diagnostic method and chemotherapy for stomach cancer cancerated by EBV.

For screening of a chemotherapeutic agent for stomach cancer cancerated by EBV and for establishing a cell line for stable production of EBV-related antigens, the present inventors speculated that a cell line can be established from stomach cancer tissues reflecting in vivo canceration and having stable traits as cancer.

Accordingly, stomach cancer tissues obtained by removing cancer lesions were treated with an antibiotic and then cultured in MEM medium mixed with an equal volume of keratinocyte-SFM and supplemented with 10% inactivated fetal calf serum and as a result of their eager study, the present inventors succeeded in establishing the stomach cancer cell line GTC-4 to arrive at the present invention.

The established GTC-4 cells stably produce EBV related antigens and causes formation of tumors in immunodeficient mice and further causes metastasis to lymph nodes, so the cells are applicable to an vitro and in vivo screening of an anticancer drug targeted at EBV-infected stomach cancer cells.

Further, upon infection of epithelial cells with a culture supernatant of GTC-4, expression of the EBV-related antigen VCA was observed while cytopathic effect (CPE) was brought about, and GTC-4 was thus confirmed to produce EBV infecting epithelial cells. The EBV can be used for analysis of the mechanism of canceration by EBV as well as for screening of a drug that inhibits the growth of cancer cells by inhibiting the mechanism of canceration.

Further, GTC-4 cells produce the EBV-related antigen stably in a large amount and thus can be used as cells for production of the EBV-related antigen for use in a diagnostic drug for stomach cancer cancerated by EBV and as cells for preparation of mRNA and cDNA coding for the EBV-related antigen in the case of production of the EBV-related antigen by genetic recombination means.

That is, the present invention relates to a method of establishing an EBV-infected stomach cancer cell line by use of EBV-infected stomach cancer tissues; an EBV infected stomach cancer cell line obtained in the method; the EBV-infected stomach cancer cell line GTC-4; and a method of screening an anticancer agent by use of the EBV-infected stomach cancer cell line. Further, the present invention relates to EBV infecting epithelial cells; the EBV separated from epithelial cells; the EBV separated from GTC-4; a method of screening an antiviral agent by use of the EBV; and a method of screening an anticancer agent by use of epithelial cells infected with the EBV.

Further, the present invention relates to a diagnostic drug for stomach cancer by use of an EBV-related antigen obtained from the EBV-infected stomach cancer cell line; a method of producing an EBV-related antigen which comprises the step of culturing the EBV-infected stomach cancer cell line; and the EBV-related antigen obtained in the method. Further, the present invention relates to a method of producing mRNA and then cDNA coding for the EBV-related antigen from the EBV-related stomach cancer cell line. In the present invention, the EBV-related antigen includes, but is not limited to, latent membrane protein (LMP), viral capsid antigen (VCA) and EBV nuclear antigen (EBNA).

DETAILED DESCRIPTION OF THE INVENTION

Figure 1:
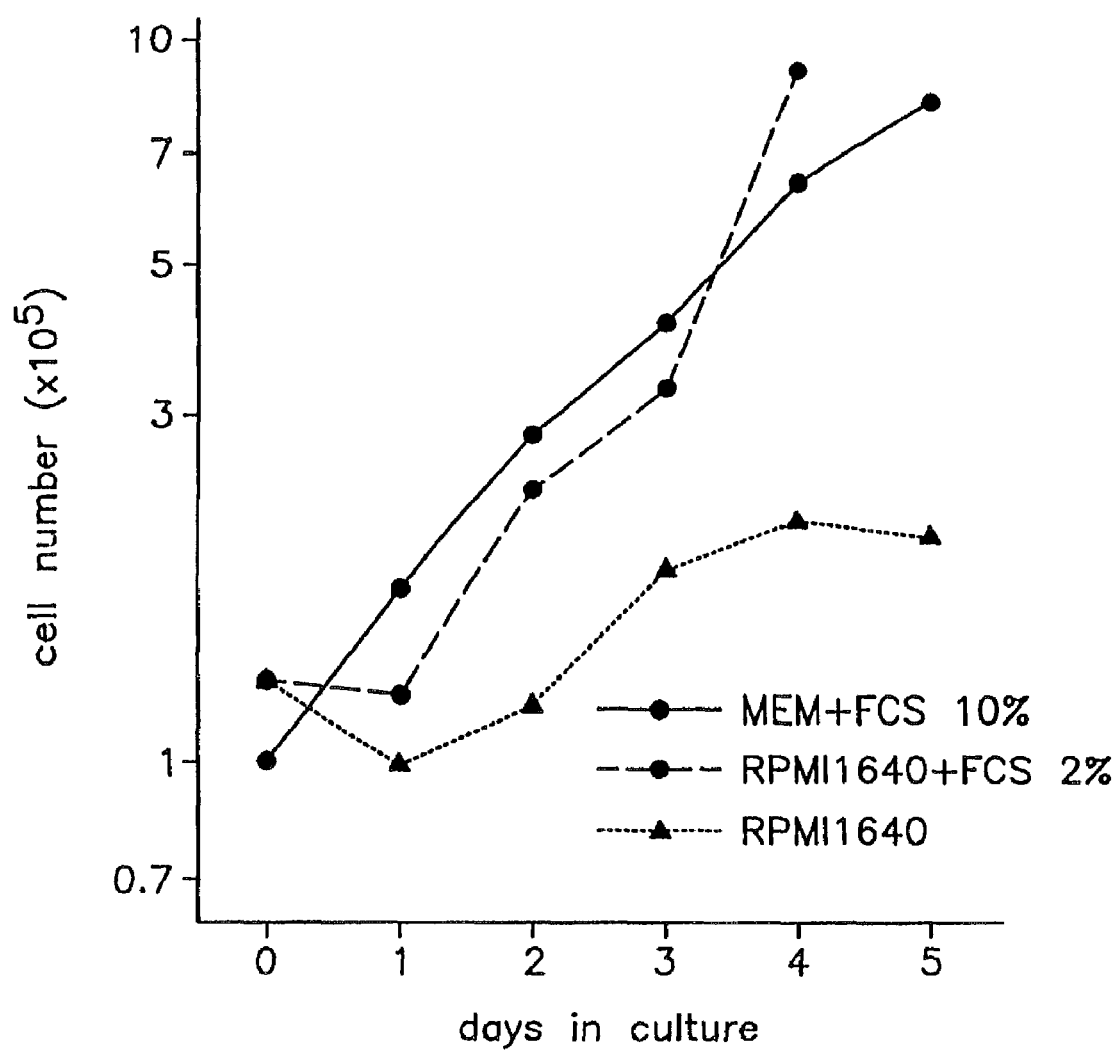
FIG. 1 is a graph showing the results of cell growth at the time of culture of GTC-4 cells in RPMI 1640 medium, RPMI 1640 medium containing 2% FCS, and MEM medium containing 10% FCS.

In the method of establishing the EBV-infected stomach cancer cell line, stomach lesions are excised from patients with stomach cancer having high antibody titer against EBV-related antigens such as VCA, with a part of EBV genes observed in the cancer tissues, and then the sample thus obtained is treated with an antibiotic, cut thin, and cultured in MEM medium mixed with an equal volume of deratinocyte-SFM and supplemented with 10% inactivated fetal calf serum. Then, the grown cells were subjected to cloning by a method of, for example, limiting dilution whereby an uniform cell line with stable expression of traits can be obtained. The resulting cell line is cultured, and the amount of produced EBV-related antigens such as LMP, VCA and EBNA is determined by a fluorescent antibody technique whereby a clone highly producing the EBV-related antigens stably can be selected.

The resulting cell line can be subjected to subculture and screening for a chemotherapeutic agent for stomach cancer caused by infection with EBV. Specifically, the cell line is cultured for a predetermined period in the presence of a drug to be examined, and the number of alive cells is evaluated by, for example, the MTT method (Carmichael et al., Cancer Res. 47,936–942, 1987) whereby a drug selectively inhibiting the growth of the cell line can be selected. Alternatively, the amount of EBV gene products such as LMP, VCA, EBNA, and EBV-derived IL-10 can be determined in an immunochemical method whereby a drug inhibiting production of the EBV gene products can be selected.

Further, after the cell line is transplanted into an immunodeficient mouse such as nude mouse treated with cyclosporin, a drug to be examined is administered at a predetermined dose into the mouse, and then the size of tumor, as well as the number and size of metastasized lesions, is examined and whether the mouse is alive or not is observed so that the effect of the drug can be judged.

The cell line is used as cells producing EBV infecting epithelial cells and hence can be used for screening of an antiviral agent inhibiting the growth of EBV in the epithelial cells. Specifically, by layering a culture supernatant of the cell line on epithelial cells such as HeLa cells, the cells are infected with EBV and then cultured for a predetermined time in the presence of a drug to be examined, and the CPE is observed under a microscope, or the expressed EBV-related antigen is detected by an immunochemical technique such as fluorescent-antibody technique or ELISA, or the EBV gene is detected by PCR etc., whereby viral growth is quantified and a drug inhibiting the growth of EBV in the epithelial cells can thus be selected.

Further, the cell line is used as cells producing EBV infecting epithelial cells and hence can be used in screening of an anticancer agent for epithelial cells cancerated by EBV. Specifically, by layering a culture supernatant of the cell line on epithelial cells such as VERO cells, the cells are infected with EBV, and cells forming colonies even in soft agar are selected and grown. The selected cell line is cultured in a predetermined time in the presence of a drug to be examined, and the number of alive cells is evaluated by, for example, the MTT method (Carmichael et al., Cancer Res. 47:936–942, 1987), and a drug selectively inhibiting the growth of the cell line can thus be selected.

The cell line, and the EBV-related antigens obtained by culturing the cell line, for example, LMP, VCA, and EBNA, can be used to examine an antibody against the EBV-related antigens in serum. For example, 1) by staining the cells by a fluorescent-antibody technique or an enzyme-anti-body technique and then observing the cells under a microscope, 2) by solubilizing the cells and then subjecting them to electrophoresis and western blotting, or 3) by ELISA using a purified or partially purified antigen from the cells, the antibody against the EBV-related antigens in serum can be examined. A specific example of each operation is shown below.

1) Fluorescent antibody technique or enzyme-antibody technique: The resulting cell line was fixed as such in ethanol or formalin, and suitably diluted serum to be examined is reacted with it and sufficiently washed. Anti-human Ig antibody labeled with fluorescence or anti-human Ig antibody labeled with an enzyme is reacted with it, and whether the EBV-related antigen expressed in the cell line is stained or not is judged by observation under a microscope.

2) Western blotting: The resulting cell line is solubilized in a sample buffer containing SDS and then subjected to SDS-PAGE, and the electrophoresed antigen is transferred onto a nitrocellulose membrane etc. The membrane is reacted with suitably diluted serum to be examined, then sufficiently washed, reacted with enzyme-labeled anti-human Ig antibody, and colored by adding a substrate. Whether a band corresponding to the molecular weight of the EBV-related antigen is stained or not is judged 3) ELISA: The resulting cell line is cultured and solubilized by, for example, a buffer containing a detergent, and the EBV-related antigen is purified by a suitable combination of conventional techniques such as chromatography, electrophoresis and gel filtration. Preferably, techniques such as antibody-affinity chromatography are desirably used. A cup or beads are coated with the purified or partially purified EBV-related antigen and then reacted with a suitably diluted serum to be examined. It is reacted with enzyme-labeled anti-human Ig antibody and then colored by adding a substrate, and from the degree of coloration, the antibody titer is evaluated. Alternatively, RI-labeled antibody may be used in place of the enzyme-labeled antibody so that the antibody titer is determined by radioactivity. If purification of the antigen is difficult, for example, an antigen capture technique using a mouse monoclonal antibody against EBV-related antigen can also be used.

Further, mRNA can be extracted from the resulting cell line by a method described in, for example, Molecular Cloning, 2nd, J. Sambrook et al., Cold Spring Harbor Laboratory Press, 1989. Then, cDNA coding for the EBV-related antigen can be obtained from the mRNA by any method known to those skilled in the art, for example, by RT-PCP using a primer selected on the basis of information on the nucleotide sequence of the EBV gene described in Arrand. J. R. et al.: Nucleic Acids Res, 9(13):2999–3014 (1981).

Further, the cDNA coding for the EBV-related antigen is inserted into a suitable expression vector, and the vector is introduced into suitable cells and the resulting transformant is cultured, and the expressed EBV-related antigen can be purified from the cell lysate. The vector into which the cDNA is inserted is not particularly limited and includes, for example, cloning vectors such as pBlueScript and pGEM and expression vectors for mammalian cells, such as pGEM-BOS, pSR$^\alpha$, and pCMV.

The host cells to which the vector is introduced is not particularly limited insofar as the cells are suitable for expression of the EBV-related antigen, and the various animal cells include, for example, established cell lines such as COS cells and PC12 cells in addition to natural cells, and further microorganisms, yeasts and insect cells can also be used. Introduction of the vector into host cells can be carried out according to the technique described in, for example, Molecular Cloning: A Laboratory, Manual, Cold Spring Harbor Laboratory, Cold Spring Harbor Laboratory Press, 1989.

The EBV-related antigen expressed in the transformant can be purified by a combination of a wide variety of conventional techniques such chromatography, electrophoresis and gel filtration. Further, if the EBV-related antigen is expressed as a fusion protein with GST or Hisb, the fusion proteins can also be purified by a glutathione-Sepharose column and nickel-Sepharose column respectively.

The GTC-4 cells according to the present invention can be stored at −80° C. or less and maintained in the Central Examination Division in a hospital attached to Teikyo University and is made available. Further, the GTC-4 cells of the invention have been deposited under Accession No. 99 012 705 since Jan. 27, 1999 with ECACC (European Collection of Cell Culture) CAMR at Porton Down, Salisbury, Wiltshire SP4 OJG, United Kingdom.

As described above, EBV-infected stomach cancer cell line GTC-4 was established from stomach cancer tissues excised from cancer lesions, and a cell line stably producing EBV-related antigens could be obtained. According to the present invention, it became possible to screen an anticancer agent by the EBV-infected stomach-cancer cells and to develop a serum diagnostic drug for stomach cancer by the EBV-related antigen.

EXAMPLES

Hereinafter, the present invention is described in more detail by reference to the examples, which however are nor intended to limit the present invention.

Example 1

Establishment of GTC-4 Cells

A cancer lesion was excised from a 70-year-old man with fragments of EBV-LMP and EBV genes observed in cancer tissues of low-differentiated adenocarcinoma, carrying 640-fold EBV-VCA antibody titer, and then the sample was treated with an antibiotic, and cultured in MEM medium mixed with an equal volume of keratinocyte-SFM and supplemented with 10% inactivated fetal calf serum, to establish stomach cancer cell line GTC-4 producing EBV-related antigen.

The established GTC-4 was cultured on a cover glass, fixed in methanol or formalin and stained with an antibody against, markers for epithelial or mononuclear cells or with a monoclonal antibody against the EBV-related antigen.

As a result, GTC-4 cells were stained with epithelial cell markers such as cytokeratin, epithelial membrane antigen (EMA) and carcinoembryonic antigen (CEA) but were not stained with antibodies against mononuclear cell markers CD45, CD49, CD3 and M3F. From expression of these markers, GTC-4 was found to be that derived from epithelial cells.

Further, GTC-4 cells were stained strongly with the EBV-related antigens LMP-1, VCA and EBNA-1, and it was thus confirmed that EBV-related antigens were produced in higher yield.

Further, the cells were dissolved in a sample buffer containing SDS and subjected to immunoblotting after SDS-PAGE in 10–20% linear gradient gel. As a result, it was found that GTC-4 cells expressed LMP-1 protein in a larger amount than by B95–8, Raji and GT-38.

Example 2

Examination of Culture Conditions for GTC-4 Cells

GTC-4 cells were cultured in RPMI 1640 medium, RPMI 1640 medium containing 2% FCS, and MEM medium containing 10% FCS. The results are shown in FIG. 1. As is evident from FIG. 1, growth of the cells was better in RPMI 1640 medium containing 2% FCS than in MEM medium containing 10% FCS, and their growth was observed even in FCS-free RPMI 1640. However, the amount of VCA antigen produced was lower in RPMI 1640 medium containing 2% FCS in which good growth was observed. VCA antigen was produced best in MEM, medium containing 10% FCS, and its production was stable.

Example 3

Transplantation of GTC-4 into Nude Mice

Two weeks after 0.25 mg/mouse cyclosporin was administered into nude mice (BALB/c/nu/nu), $4 \times 10^7$ GTC-4 cells were transplanted. Two months later, swelling was observed in the site of transplantation, and 4 months later when the mice were dissected, metastasized lesions were observed in the peritoneum. The metastasized tissues were transplanted into 5-week-old nude mice to which cyclosporin had been administered in the same manner, and 3 months later, swelling was observed in the lymph nodes.

Example 4

Infection of Epithelial Cells with EBV in Culture Supernatant of GTC-4 Cells

By treating GTC-4 cells with TPA and n-butylate, production of EBV particles was observed. This culture supernatant was inoculated onto epithelial cells (VERO cells) and 4 days later, specific positive staining reaction with anti-VCA antibody was observed in nuclei of many cells.

What is claimed is:

1. A method of screening a potential anticancer agent which comprises,
    culturing GTC-4 (Budapest Treaty Deposit Accession No. 99012705) cells in the presence of a potential anticancer agent and
    determining the effects of the potential anticancer agent on growth of the GTC-4 cells,
    wherein an inhibition in growth of the GTC-4 cells is due to the activity of the anticancer agent.

* * * * *